US00PP21791P2

(12) United States Plant Patent
Sakazaki

(10) Patent No.: US PP21,791 P2
(45) Date of Patent: Mar. 15, 2011

(54) *LOBELIA* PLANT NAMED 'USLOB0901'

(50) Latin Name: *Lobelia hybrida*
Varietal Denomination: USLOB0901

(75) Inventor: Ushio Sakazaki, Shiga (JP)

(73) Assignee: Plant 21 LLC, Bonsall, CA (US)

( * ) Notice: Subject to any disclaimer, the term of this patent is extended or adjusted under 35 U.S.C. 154(b) by 0 days.

(21) Appl. No.: 12/653,760

(22) Filed: Dec. 16, 2009

(51) Int. Cl.
*A01H 5/00* (2006.01)

(52) U.S. Cl. ..... Plt./451

(58) Field of Classification Search ..... Plt./451
See application file for complete search history.

(56) References Cited

U.S. PATENT DOCUMENTS

PP16,112 P3 * 11/2005 Oud ..... Plt./451
PP19,680 P2 * 2/2009 Klemm ..... Plt./451

OTHER PUBLICATIONS

UPOV ROM GTITM Computer Database GTI Jouve Retrieval Software 2010/03 Citation for 'USLOB0901'.*

* cited by examiner

*Primary Examiner*—Wendy C. Haas
(74) *Attorney, Agent, or Firm*—C. A. Whealy

(57) ABSTRACT

A new and distinct cultivar of *Lobelia* plant named 'USLOB0901', characterized by its compact, upright to outwardly spreading plant habit; freely branching habit; continuously and freely flowering habit; dark blue-colored flowers; and relatively high temperature tolerant.

1 Drawing Sheet

Botanical designation: *Lobelia hybrida.*
Cultivar denomination: 'USLOB0901'.

BACKGROUND OF THE INVENTION

The present invention relates to a new and distinct cultivar of *Lobelia* plant, botanically known as *Lobelia hybrida* and hereinafter referred to by the name 'USLOB0901'.

The new *Lobelia* plant is a product of a planned breeding program conducted by the Inventor in Higashiomi, Shiga, Japan. The objective of the breeding program is to create new uniform *Lobelia* cultivars with good vigor, attractive and stable flower coloration and tolerance to high temperatures.

The new *Lobelia* plant originated from a cross-pollination made by the Inventor on Sep. 26, 2005 of *Lobelia hybrida* 'Hot Water Blue', not patented, as the female, or seed, parent with *Lobelia hybrida* 'Dark Blue Angel', not patented, as the male, or pollen, parent. The new *Lobelia* plant was discovered and selected by the Inventor as a single flowering plant with the progeny of the stated cross-pollination grown in a controlled greenhouse environment in Higashiomi, Shiga, Japan on Aug. 28, 2006.

Asexual reproduction of the *Lobelia* plant by vegetative cuttings in Higashiomi, Shiga, Japan since Sep. 2, 2006, has shown that the unique features of this new *Lobelia* plant are stable and reproduced true to type in successive generations.

SUMMARY OF THE INVENTION

Plants of the new *Lobelia* have not been observed under all possible environmental conditions. The phenotype may vary somewhat with variations in environment such as temperature and light intensity without, however, any variance in genotype.

The following traits have been repeatedly observed and are determined to be the unique characteristics of 'USLOB0901'.

These characteristics in combination distinguish 'USLOB0901' as a new and distinct cultivar of *Lobelia:*

1. Compact, upright to outwardly spreading plant habit.
2. Freely branching habit.
3. Continuously and freely flowering habit.
4. Dark blue-colored flowers.
5. Relatively high temperature tolerant.

Plants of the new *Lobelia* differ from plants of the female parent, 'Hot Water Blue', in the following characteristics:

1. Plants of the new *Lobelia* are more compact than and not as open as plants of 'Hot Water Blue'.
2. Plants of the new *Lobelia* have darker blue-colored flowers than plants of 'Hot Water Blue'.

Plants of the new *Lobelia* differ from plants of the male parent, 'Dark Blue Angel' in the following characteristics:

1. Plants of the new *Lobelia* have more mounding habit than plants of 'Dark Blue Angel'.
2. Plants of the new *Lobelia* and 'Dark Blue Angel' differ in flower color as plants of 'Dark Blue Angel' have purple-colored flowers.

Plants of the new *Lobelia* can be compared to plants of *Lobelia* 'Regatta Sapphire', not patented. In side-by-side comparisons conducted in Bonsall, Calif., plants of the new *Lobelia* differed from plants of 'Regatta Sapphire' in the following characteristics:

1. Plants of the new *Lobelia* were more compact than and not as open as plants of 'Regatta Sapphire'.
2. Plants of the new *Lobelia* had darker blue-colored flowers than plants of 'Regatta Sapphire'.
3. Plants of the new *Lobelia* were more high temperature-tolerant than plants of 'Regatta Sapphire'.

Plants of the new *Lobelia* can also be compared to plants of *Lobelia* 'Fountain Blue', not patented. In side-by-side comparisons conducted in Bonsall, Calif., plants of the new *Lobelia* differed from plants of 'Fountain Blue' in the following characteristics:

1. Plants of the new *Lobelia* were more freely branching than plants of 'Fountain Blue'.
2. Plants of the new *Lobelia* were more high temperature-tolerant than plants of 'Fountain Blue'.

BRIEF DESCRIPTION OF THE PHOTOGRAPHS

The accompanying colored photographs illustrate the overall appearance of the new *Lobelia* plant, showing the colors as true as it is reasonably possible to obtain in colored reproductions of this type. Colors in the photographs may differ slightly from the color values cited in the detailed botanical description which accurately describe the actual colors of the new *Lobelia* plant.

The photograph at the bottom of the sheet comprises a side perspective view of a typical flowering plant of 'USLOB0901' grown in a container.

The photograph at the top of the sheet is a close-up view of typical flowers of 'USLOB0901'.

DETAILED BOTANICAL DESCRIPTION

Plants used for the aforementioned photographs and following description were grown under conditions which closely approximate commercial production conditions during the autumn in 12.5-cm containers in an outdoor nursery in Bonsall, Calif. During the production of the plants, day temperatures ranged from 18° C. to 38° C., night temperatures ranged from 9° C. to 18° C. and light levels ranged from 7,000 to 10,000 foot-candles. Plants were pinched one time and were seven weeks old when the photographs and description were taken. In the following description, color references are made to The Royal Horticultural Society Colour Chart, 2007 Edition, except where general terms of ordinary dictionary significance are used.

Botanical classification: *Lobelia hybrida* 'USLOB0901'.

Parentage:

*Female parent.*—*Lobelia hybrida* 'Hot Water Blue', not patented.

*Male parent.*—*Lobelia hybrida* 'Dark Blue Angel', not patented.

Propagation:

*Type cutting.*—Vegetative tip cuttings.

*Time to initiate roots, summer.*—About four days at temperatures ranging from 17° C. to 29° C.

*Time to initiate roots, winter.*—About six days at temperatures ranging from 17° C. to 21° C.

*Time to produce a rooted plant, summer.*—About 22 days at temperatures ranging from 17° C. to 29° C.

*Time to produce a rooted plant, winter.*—About 25 days at temperatures ranging from 17° C. to 21° C.

*Root description.*—Medium in thickness, fibrous; white in color.

*Rooting habit.*—Moderate branching; medium in density.

Plant description:

*Form.*—Compact, upright to outwardly spreading plant habit; freely branching habit with about 15 lateral branches per plant each primary lateral developing multiple secondary laterals, pinching enhances lateral branch development; moderately vigorous growth habit.

*Plant height.*—About 14 cm.

*Plant width.*—About 26 cm.

*Lateral branch description.*—Length: About 13 cm. Diameter: About 2 mm. Internode length: About 1.5 cm. Strength: Strong, flexible. Texture: Smooth, glabrous. Color: Close to 146A.

Foliage description:

*Arrangement.*—Alternate, simple; sessile.

*Length.*—About 3.8 cm.

*Width.*—About 8 mm.

*Shape.*—Oblanceolate to lanceolate.

*Apex.*—Acute.

*Base.*—Attenuate.

*Margin.*—Shallowly and sparsely serrated.

*Texture, upper and lower surfaces.*—Smooth, glabrous.

*Venation pattern.*—Pinnate; arcuate.

*Color.*—Developing leaves, upper surface: Close to 137A. Developing leaves, lower surface: Close to 146B. Fully expanded leaves, upper surface: Close to 137B; venation, close to 137B. Fully expanded leaves, lower surface: Close to 146B; venation, close to 137C.

Flower description:

*Flower arrangement, form and habit.*—Solitary axillary flowers with three broad lower (two laterals and one lip) petals and two narrower upper (banner) petals, petals fused towards the base into a narrow tube; freely flowering habit with about 21 to 22 flowers and flower buds per lateral stem at one time; flowers face upright to outwardly.

*Natural flowering season.*—Under greenhouse conditions, plants begin flowering about seven weeks after planting. Under outdoor conditions, plants begin flowering during the spring and flower continuously until frost in California; flowering indeterminate with new flowers overgrowing older flowers and leaves.

*Flower longevity on the plant.*—Longevity of individual flowers is highly dependent on environmental conditions; flowers typically last about three to four days on the plant; flowers persistent.

*Fragrance.*—None detected.

*Flower buds.*—Length: About 9 mm. Diameter: About 3 mm. Shape: Obovate. Color: Close to N77C.

*Flower size.*—About 1.7 cm.

*Flower depth (height).*—About 2 cm.

*Flower throat diameter.*—About 2.5 mm.

*Flower tube length.*—About 8 mm.

*Flower tube diameter at base.*—About 1.5 mm.

*Petals.*—Arrangement: Single whorl of five petals, petals fused at the base into a narrow tube; three broad lower (two laterals and one lip) petals and two narrower upper (banner) petals. Three lower petals: Lobe length: About 8 mm. Lobe width: About 6 mm. Shape: Obovate. Apex: Rounded. Margin: Entire. Texture, upper and lower surfaces: Smooth, glabrous; velvety. Two upper petals: Lobe length: About 6 mm. Lobe width: About 1.5 mm. Shape: Lanceolate. Apex: Rounded. Margin: Entire. Texture, upper and lower surfaces: Smooth, glabrous; velvety. Color, all petals: When opening, upper surface: Close to 97B to 97C. When opening, lower surface: Close to 97D. Fully opened, upper surface: Close to 99C; towards the base, close to NN155D; central spots, close to N144B; nectar guides, close to 99A; color does not fade with development. Fully opened, lower surface: Close to 96D; color does not fade with development. Throat: Close to 100D; tiny flecks, close to 100C. Tube: Close to 100B to 100C.

*Sepals.*—Arrangement: Single whorl of five sepals, fused at the base; star-shaped calyx. Length: About 7 mm. Width: About 1 mm. Shape: Lanceolate. Apex: Acute. Margin: Entire. Texture, upper and lower surfaces: Smooth, glabrous. Color, upper surface: Close to 147A. Color, lower surface: Close to 147B.

*Peduncles.*—Length: About 1.8 cm. Diameter: About 1 mm. Aspect: About 45° from the lateral stem axis. Strength: Moderately strong, flexible. Texture: Pubescent. Color: Close to 147A.

*Reproductive organs.*—Stamens: Quantity per flower: About five. Filament length: About 5 mm. Filament color: Close to 95C. Anther length: About 2 mm. Anther shape: Lanceolate. Anther color: Close to 202B. Pollen amount: Scarce. Pollen color: Close to 155D. Pistils: Quantity per flower: One. Pistil length: About 8 mm. Stigma shape: Round. Stigma color: Close to 96D. Style length: About 5 mm. Style color: Close to 145C. Ovary color: Close to 144A.

*Seeds/fruits.*—Seed and fruit development have not been observed.

Disease/pest resistance: Plants of the new *Lobelia* have not been noted to be resistant to pathogens and pests common to *Lobelia*.

Temperature tolerance: Plants of the new *Lobelia* have been observed to tolerate temperatures from about 1° C. to about 40° C.; relatively high temperature tolerant.

It is claimed:

1. A new and distinct *Lobelia* plant named 'USLOB0901' as illustrated and described.

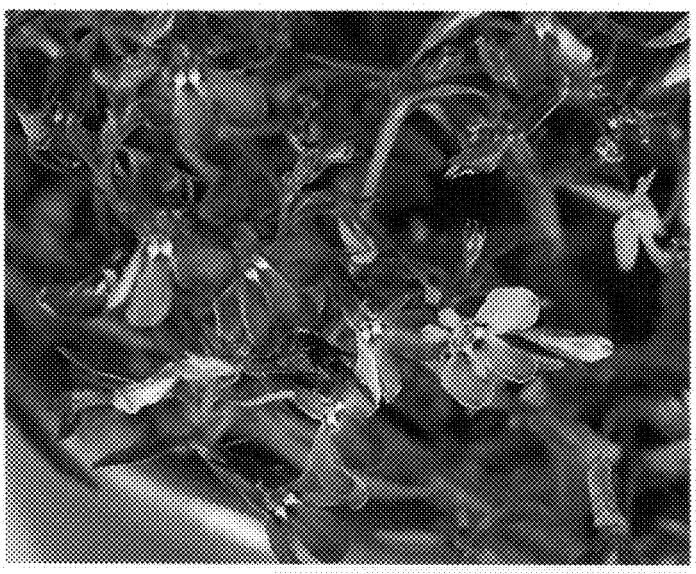
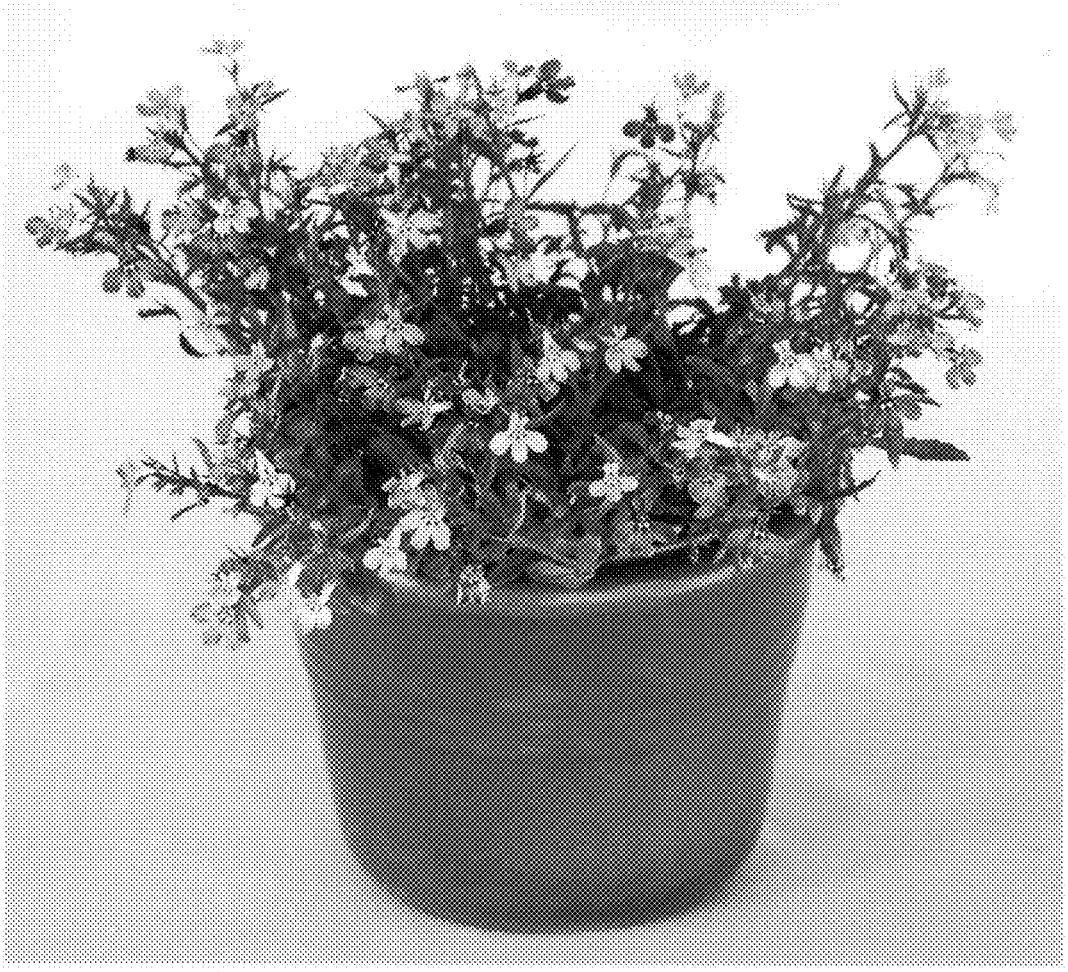

* * * * *